United States Patent [19]

Morishita et al.

[11] Patent Number: 4,695,466
[45] Date of Patent: Sep. 22, 1987

[54] MULTIPLE SOFT CAPSULES AND PRODUCTION THEREOF

[75] Inventors: Takashi Morishita, Nishinomiya; Takehisa Hata, Muko; Mitio Mori, Higashiosaka; Shohachi Tanoue, Toyonaka, all of Japan

[73] Assignees: Morishita Jintan Co., Ltd.; Fujisawa Pharmaceutical Co., Ltd., both of Osaka, Japan

[21] Appl. No.: 931,940

[22] Filed: Nov. 18, 1986

Related U.S. Application Data

[63] Continuation of Ser. No. 570,289, Jan. 13, 1984, abandoned.

[30] Foreign Application Priority Data

Jan. 17, 1983 [JP] Japan .................................. 58-6287

[51] Int. Cl.⁴ ........................... A61J 3/07; A61K 9/54
[52] U.S. Cl. ..................................... 424/456; 424/451; 424/458; 424/460; 424/461; 426/89; 426/138; 426/140
[58] Field of Search ....................... 424/16, 19, 20, 21, 424/31, 34, 37; 426/89, 138, 140; 427/2, 3

[56] References Cited

U.S. PATENT DOCUMENTS

| 3,275,519 | 9/1966 | Glassman | 424/37 |
| 3,664,963 | 5/1972 | Pasin | 424/37 |
| 4,394,287 | 7/1983 | Scarpelli | 424/37 |
| 4,532,123 | 7/1985 | Gardner | 424/19 |

FOREIGN PATENT DOCUMENTS

| 2729068 | 1/1979 | Fed. Rep. of Germany . |
| 3030801 | 4/1981 | Fed. Rep. of Germany . |
| 715879 | 9/1954 | United Kingdom . |
| 1538510 | 1/1979 | United Kingdom . |
| 1564452 | 4/1980 | United Kingdom . |

Primary Examiner—John Kight
Assistant Examiner—Nathan M. Nutter
Attorney, Agent, or Firm—Oblon, Fisher, Spivak, McClelland & Maier

[57] ABSTRACT

The present invention relates to a multiple soft capsule in which a soft capsule is contained in another soft capsule and the production thereof. The multiple soft capsule is useful for various industrial fields such as medicine, foods, table luxuries and the like. Especially, the multiple capsule is useful in medical field, for instance, in combining two or more components which cannot be enclosed together in a single capsule or in the dissolution control in vivo of the medicines by properly selecting the kind of the film-forming substance for the outer and inner soft capsules.

4 Claims, 4 Drawing Figures

MULTIPLE SOFT CAPSULES AND PRODUCTION THEREOF

This application is a continuation of application Ser. No. 570,289 filed on Jan. 13, 1984, now abandoned.

BACKGROUND OF THE INVENTION

Figure 1:
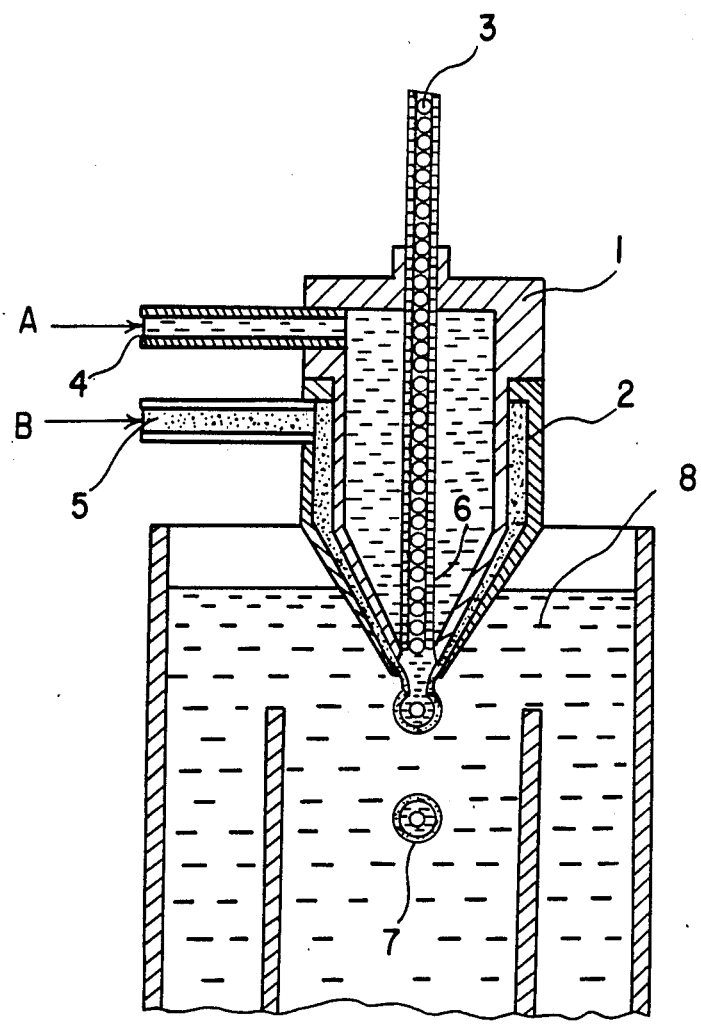
FIGS. 1 and 2 are schematic vertical sectional views illustrating the embodiments of nozzle part for producing a multiple soft capsule.

Various softencapsulated medicines, foods, table luxuries and the like are widely on the market, and as those containing solid fillers therein, there are known oily soft capsules in which solid and oil agents are encapsulated with a capsule film-forming substance consisting mainly of gelatin (refer to Japanese Patent Publication No. 42044/1982). However, a multiple soft capsule in which one or more inner soft capsules are contained together with a liquid material in an outer soft capsule is not previsously known.

SUMMARY OF THE INVENTION

The present invention provides multiple soft capsules containing one or more inner soft capsules in an outer soft capsule, which are especially useful in combining two or more components which cannot be enclosed together in a single capsule or in the regulation of the rate of dissolution in vivo of the medicines by properly selecting the kind of the film-forming substance for the outer and inner soft capsules.

DETAILED DESCRIPTION OF THE INVENTION

The present invention relates to novel multiple soft capsules in which a soft capsule is contained in another soft capsule.

Hitherto, various softencapsulated medicines, foods, table luxuries, etc. are widely on the market, and as those containing solid fillers therein, there are known oily soft capsules in which solid and oil agents are enclosed with a capsule film-forming substance consisting mainly of gelatin (refer to Japanese Patent Publication No. 42044/1982).

The present inventors found that the use of softencapsulated products is markedly extended by causing a soft capsule to contain another soft capsule therein, and thus attained to the present invention.

The gist of the present invention is to provide multiple soft capsules in which one or more inner soft capsules are contained in an outer soft capsule.

The film-forming substance of the soft capsules, either inner soft capsule or outer one, used in the present invention is not particularly limited, but as preferred substances, there are given, for example, those containing gelatin alone as an essential component; those containing (a) gelatin, (b) a water-soluble polyhydric alcohol or its water-soluble derivative as an essential component; or those which are obtained by treating a composition containing (a) gelatin, (b) a water-soluble polyhydric alcohol or its water-soluble derivative and (c) a lower methoxylpectin or sodium alginate with a compound capable of geletinizing an aqueous solution of lower methoxylpectin or sodium alginate, and the like.

Of the film-forming substances for the soft capsules, as to gelatin and the water-soluble polyhydric alcohol or its water-soluble derivative, those of a grade so far used for producing soft capsules may be used as such.

As the water-soluble polyhydric alcohol or its water-soluble derivative, there are given, for example, glycerin, polyglycerin, sorbite, ethylene glycol, polyethylene glycol, propylene glycol, polypropylene glycol, ethylene oxide/propylene oxide copolymer, oligosaccharide, sugar ester, glyceride, sorbitan ester and the like, which are not however to be regarded as limitative.

When gelatin and the water-soluble polyhydric alcohol or its water-soluble derivative are used as a film-forming substance for soft capsule, it is preferred that the amount of gelatin used and that of the water-soluble polyhydric alcohol or its water-soluble derivative used are 60 to 90 weight % and 10 to 40 weight %, respectively, based on the total weight of the capsule film.

When gelatin, a lower methoxylpectin and the water-soluble polyhydric alcohol or its water-soluble derivative are used as a film-forming substance for soft capsule, it is preferred that the amounts of the first, second and the latter used are 65 to 75 weight %, 5 to 20 weight %, preferably 10 to 15 weight %, and 10 to 30 weight %, respectively, based on the total weight of the capsule film.

When gelatin, sodium alginate and the water-soluble polyhydric alcohol or its water-soluble derivative are used as a film-forming substance for soft capsule, it is preferred that the amounts of the first, second and the latter used are 65 to 85 weight %, 1 to 10 weight %, preferably 3 to 5 weight % and 10 to 30 weight %, respectively, based on the total weight of the capsule film.

A preferred lower methyoxylpectin is those in which the molecular weight is not less than 200,000 and the degree of methoxylation is 1 to 6 %, particularly 3.5 to 5 %.

As the compound capable of gelatinizing aqueous solutions of a lower methoxylpectin or sodium alginate, there may properly be used the salt of polyvalent metals having two or more valences, particularly the water-soluble salts of calcium, magnesium, etc. for a lower methoxylpectin, and water-soluble calcium salts such as calcium chloride, calcium phosphate, etc. for sodium alginate.

The multiple soft capsule according to the present invention may be used, in addition to those which are taken orally such as medicines, foods, table luxuries, etc., for those which are applied to industrial uses such as various industrial products (e.g. two-component type adhesives, etc.), feeds, agricultural and horticultural chemicals, cosmetics, medical supplies and the like. Consequently, the film-forming substance for the inner and outer soft capsules, kind of liquors to be encapsulated in the inner soft capsule (the liquor is shorten as an inner capsule liquor hereinafter), size of the capsules, number of the inner soft capsules contained and the like may properly be selected according to the object of use and usages.

The multiple soft capsule according to the present invention is suitable in the fields of medicines, foods and table luxuries, particularly in the field of medicines.

When the multiple soft capsule is medicines, the rate of dissolution in vivo of the medicines can be regulated by properly selecting the kind of the film-forming substance for the outer and inner soft capsules.

For example, by making the film of the outer soft capsule soluble at the stomach by preparing the film from the foregoing film-forming components (a) and (b), and by making the film of the inner soft capsule soluble at the intestine by preparing the film from the foregoing film-forming components (a), (b) and (c), various excellent effects can be obtained, for example, the efficacy of medicines can be maintained in vivo, or medicines can be protected from decomposition b gastric juice.

Next, production of the multiple soft capsule according to the present invention will be illustrated with reference to the accompanying drawings.

FIG. 1 is a schematic vertical sectional view illustrating one embodiment of the nozzle part of a suitable equipment for producing the multiple soft capsule according to the present invention.

The multiple soft capsule (7) according to the present invention is obtained as follows:

An inner soft capsule (3) (containing a proper inner capsule liquor) sent to the nozzle part, and an outer capsule liquor (4) to be filled in an outer soft capsule, as sent from A and passed through a slit (6), are pushed together out of the ring-form tip of an inner nozzle (1), and at the same time therewith, an outer film-forming liquor (5) for the outer soft capsule, as sent from B, is pushed out of the ring-form tip of an outer nozzle (2) arranged outside said ring-form tip and in the form of concentric circle, thereby to form a double jet which is then discharged into a cooling liquor (8).

In this case, when the inner soft capsule (3) is a double soft capsule, a triple soft capsule is obtained, and when it is a triple soft capsule, a quadruple soft capsule is obtained. In the same manner as above, any of desired multiple soft capsusles may be produced.

In the prior art method wherein the filler is a liquid only, the encapsulation is made easy and the particle diameter is made uniform by giving moderate perturbation to the multiple jet flow using a perturbation means to cause the flow to be cut well. In the method of the present invention described above, however, the inner soft capsule (3), on being pushed out of the tip of the nozzle, acts to pull the outer capsule liquor (4) and outer film-forming liquor (5) into the flow, so that the same effect as with the perturbation means can be given to the multiple jet flow.

Of course, in the method of the present invention, a proper perturbation means may be employed if desired according to the kind and property of the inner soft capsule and the number thereof contained.

With the multiple soft capsule produced as above using the foregoing (a) and (b) as essential components for the film of the outer soft capsule, it suffices to use a vegetable oil, mineral oil, animal oil or the like as a cooling liquor and after solidifying the capsule by cooling, to dry and wash the capsule as such.

While, with the multiple soft capsule produced as above using the foregoing (a), (b) and (c) as essential components for the film of the outer soft capsule, the capsule, after solidified by cooling, is brought into contact with a solution, preferably an aqueous solution of the compound capable of gelatinizing aqueous solutions of a lower methoxylpectin or sodium alginate. In this case, it is a common practice to dip the capsule to be treated in an aqueous solution containing 1 to 10 weight %, preferably 3 to 5 weight % of said compound at 5° C. to 30° C., preferably 10° C. to 15° C. for 1 to 5 minutes, preferably 1 to 3 minutes. The contact between the multiple soft capsule and the treating liquor may be carried out, in addition to the dipping method, by other methods such as the spraying method. But the dipping method is most simple as well as applicable uniformly. The multiple soft capsule treated as above is then dried and washed.

Figure 2:
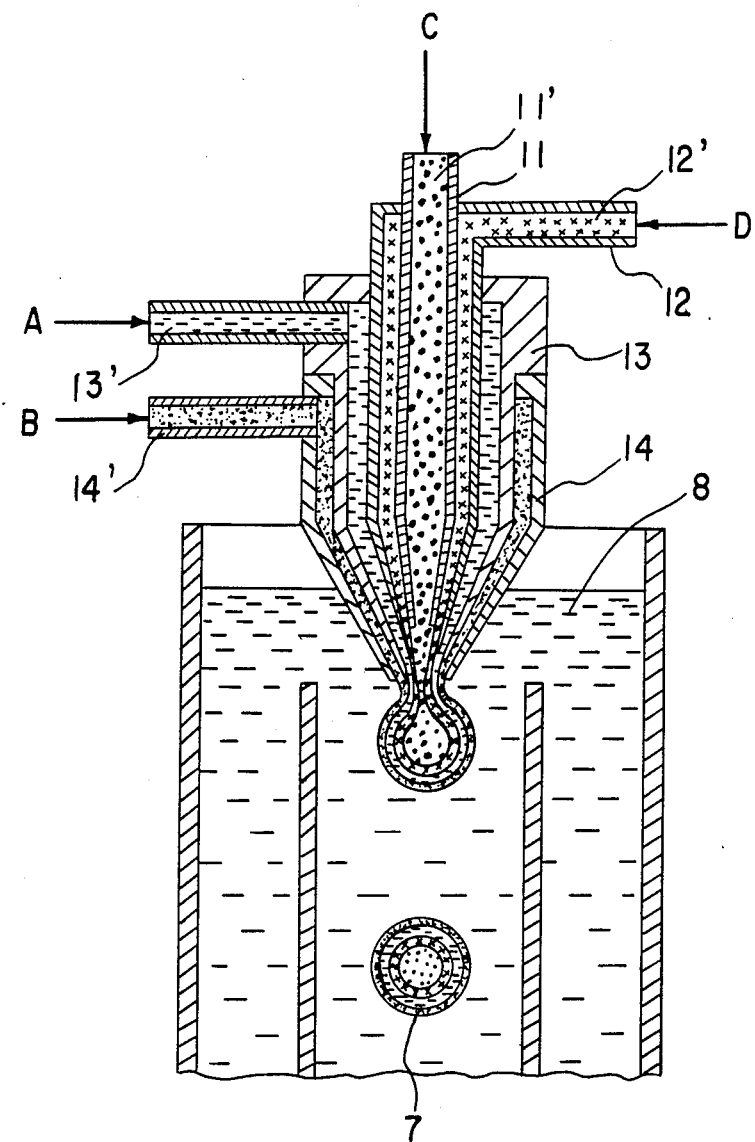

Another method suitable to produce the multiple soft capsule according to the present invention is a method characterized in that an inner capsule liquor, a film-forming liquor for the inner soft capsule (shorten as an inner film-forming liquor hereinafter), an outer capsule liquor and an outer film-forming liquor therefor are at the same time pushed out of the first nozzle, second one, third one and forth one respectively, as arranged in the form of concentric circle, having increasing radii in this order, thereby to form a multiple jet which is then discharged into a cooling liquor. FIG. 2 is a schematic vertical sectional view illustrating one embodiment of the nozzle part of an equipment for practicing this method.

In the equipment shown in FIG. 2, the multiple soft capsule (7) according to the present invention is obtained as follows:

An inner capsule liquor (11') sent from C, an inner film-forming liquor (12') sent from D, an outer capsule liquor (13') sent from A and outer film-forming liquor (14') sent from B are at the same time pushed out of the ring-form tips of the first nozzle (11), second one (12), third one (13) and fourth one (14), respectively, as arranged in the form of concentric circle, having increasing radii in this order, thereby to form a multiple jet flow which is then discharged into a cooling liquor (8).

Also in this case, with the multiple soft capsule produced using the foregoing (a) and (b) as essential components for the film of the outer soft capsule, it suffices to dry and wash the capsule as such. But, with the multiple soft capsule produced using the foregoing (a), (b) and (c) as said components, the capsule, after treated as above, is dried and washed.

The present invention extends the use of softencapsulated products in all the industrial fields, and particularly it is effective in combining two or more components which cannot be enclosed together in a single capsule because of incompatibility and the like. Further, a synergistic effect, sustained effect, etc. can also be obtained depending upon the components contained.

The aesthetic appearance of the multiple soft capsule according to the present invention is expected to contribute to extending demands for said encapsulated product. Next, the present invention will be illustrated with reference to the following examples.

EXAMPLE 1

According to the conventional method, a garlic oil-containing inner soft capsule (particle diameter, 2 mm) was prepared using an inner film-forming liquor of the following recipe.

Recipe for the inner film-forming liquor:

|  | Parts by weight |
|---|---|
| Gelatin | 16 |
| D-sorbite | 4 |
| Purified water | 80 |

Figure 3:
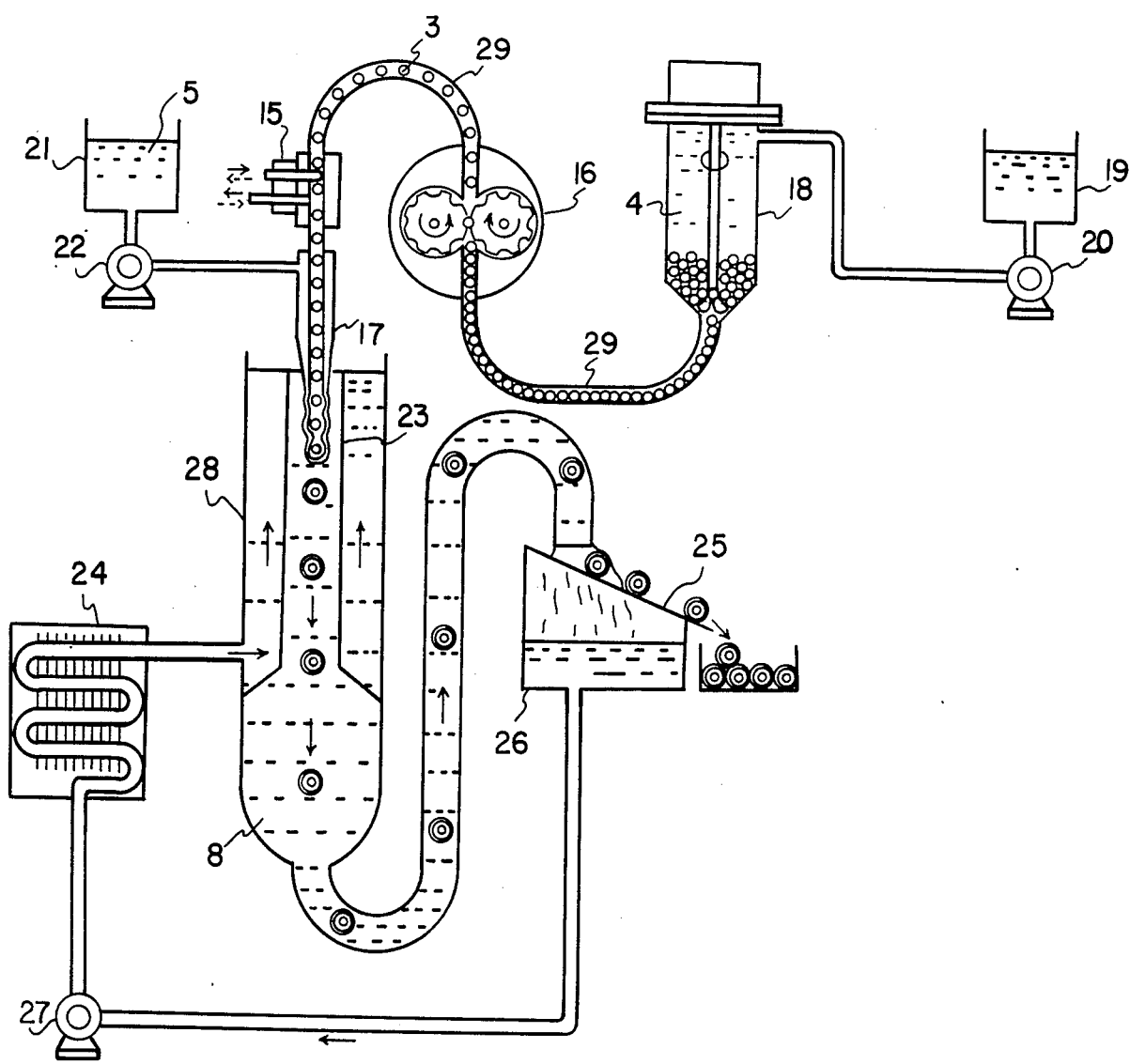
FIGS. 3 and 4 are schematic flow sheets illustrating the production of a multiple soft capsule.

According to the flow sheet shown in FIG. 3, the inner soft capsule obtained above and a vitamin E-containing oil were encapsulated together using an outer film-forming liquor for outer soft capsule of the following recipe to obtain a double capsule having an outside diameter of 6 mm.

Recipe of the outer film-forming liquor:

|  | Parts by weight |
|---|---|
| Gelatin | 16 |
| d-sorbite | 4 |
| Purified water | 80 |

The flow sheet in FIG. 3 will be illustrated later. A vitamin E-containing oil (4) (an outer capsule liquor) is sent from an outer capsule liquor storage tank (19) to an inner capsule storage tank (18) through a pump (20) to mix with inner soft capsules. The temperature of said outer capsule liquor (4) is kept constant (in this example, 20±1° C.), and the viscosity of the liquor is preferably 400 cps. The inner soft capsule (3) and the liquor (4) are sent together, at a flow rate of 0.3 ml/min., from the tank (18) through a pipe (29) (inside diameter, 2.5 mm), an extruder (16) and the pipe (29) to a double nozzle (17) (inner nozzle diameter, 3.0 mm; outer nozzle diameter, 6.0 mm). An aligning machine (15) is set between the extruder (16) and double nozzle (17) to make a distance between the inner soft capsules constant (in this example, pitch number, 2.5 mm). The number of the inner soft capsules extruded is fixed to 8/sec. While an outer film-forming liquor (5), while being maintained at a constant temperature (in this example, 60±2° C.), is sent, at a flow rate of 0.2 ml/sec, from a film-forming liquor storage tank (21) through a pump (22) to the double nozzle (17) to form a double jet which is then discharged into a cooling liquor (vegetable oil in this example). The cooling liquor (8) is kept at a low and constant temperature (9±0.5° C. in this example) by a cooler (24) and circulated by means of a pump (27), at a flow rate of 240 ml/sec, through a cooling pipe (28) (inside diameter, 120 mm; length, 1000 mm), forming pipe (23) (inside diameter, 30 mm; length, 600 mm) set in the cooling pipe (28), tank (26), pump (27) and cooler (24) in this order. The capsules formed in the forming pipe (23) are sent, together with the circulating flow of the cooling liquor (8), to a separator (25) (sieve) wherein the capsules are separated from the cooling liquor (8), and then dried and washed. The outside diameter of the outer soft capsule of the double capsule thus obtained is 6±0. 2 mm.

EXAMPLE 2

In the same manner as in Example 1, a double capsule of the following recipe was prepared.

Diameter of the inner soft capsule: 4 mm
Inner caspsule liquor:

|  | parts by weight |
|---|---|
| ethylcysteine hydrogene chloride | 30 |
| safflower oil | 70 |

Recipe for an inner film-forming liquor:

|  | parts by weight |
|---|---|
| Gelatin | 75 |
| D-sorbite | 20 |
| Sodium alginate | 5 |
| Water | 300 |

Diameter of the outer soft capsule: 8 mm
Outer capsule liquor:

|  | parts by weight |
|---|---|
| cytric acid carbetapentane | 10 |
| safflower oil | 90 |

Recipe for an outer film-forming liquor:

|  | parts by weight |
|---|---|
| Gelatin | 80 |
| D-sorbite | 20 |
| Water | 350 |

Manufacturing condition:
  Pitch of aligning machine (15): 4.5 mm
  Forming pipe (23): inside diameter, 30 mm; length, 600 mm;
  Cooling pipe (28): inside diameter, 120 mm length, 1000mm
  Pipe (29): inside diameter, 4.5 mm
Temperature of the outer film-forming liquor: 60° C.
Temperature of the outer capsule liquor: 20° C.
Temperature of the cooling liquor: 9° C.
Flow rate of the outer film-forming liquor: 0.4 ml/sec
Flow rate of the outer capsule liquor: 0.3 ml/sec
Flow rate of the cooling liquor: 240 ml/sec
Number of inner capsules extruded: 8/sec The outer soft capsule of the double capsule thus obtained is soluble at stomach and the inner soft capsule thereof is soluble at intestine, so that the efficacy of the respective medicines is displayed effectively.

EXAMPLE 3

Figure 4:
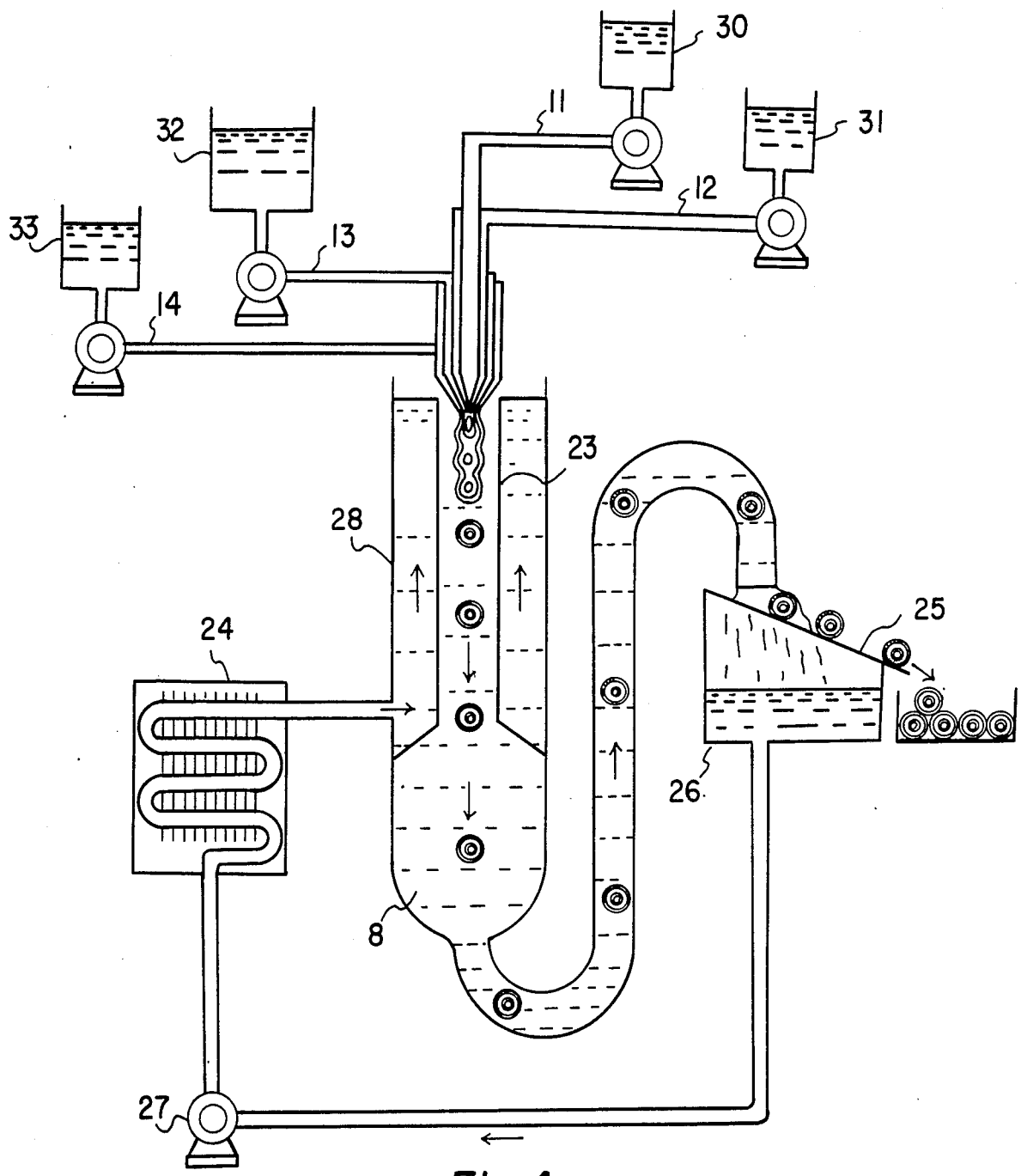

According to the flow sheet shown in FIG. 4 double capsule having an outside diameter of 8 mm is obtained.

The recipes of the capsule are as follows:
Inner capsule liquor:

|  | parts by weight |
|---|---|
| Vitamin B$_2$ | 20 |
| Safflower oil | 80 |

Inner film-forming liquor:

|  | parts by weight |
|---|---|
| Gelatin | 30 |
| Purified water | 70 |

Outer capsule liquor:

|  | parts by weight |
|---|---|
| Vitamin E | 50 |
| Wheat germ oil | 50 |

Outer film-forming liquor:

|  | parts by weight |
| --- | --- |
| Gelatin | 25 |
| D-sorbite | 5 |
| Purified water | 70 |

The above inner capsule liquor, inner film-forming liquor, outer capsule liquor and outer film-forming liquor are charged in an inner capsule liquor storage tank (30), an inner film-forming liquor storage tank (31), an outer capsule liquor storage tank (32) and an outer film-forming liquor storage tank (33), respectively, which are kept at following temperatures:

| Inner capsule liquor | 10 ± 1° C. |
| --- | --- |
| Inner film-forming liquor | 60 ± 2° C. |
| Outer capsule liquor | 20 ± 1° C. |
| Outer film-forming liquor | 60 ± 1° C. |

Every storage tank is connected with the first nozzle ($\phi$ 1.5 mm) (11), the second nozzle ($\phi$ 2.5 mm) (12), the third nozzle ($\phi$ 3 mm) (13), and the fourth nozzle ($\phi$ 5 mm) (14), respectively, to which the inner capsule liquor, inner film-forming liquor, outer capsule liquor and outer film-forming liquor are sent by pumps at flow rates of 0.5 ml/sec, 0.1 ml/sec, 1.0 ml/sec and 0.3 ml/sec, respectively, to be pushed into a cooling liquor (vegetable oil in this example) (8) stocked in a forming pipe (inside diameter: $\phi$ 30 mm, length: 600 mm) (23). The cooling liquor is circulated through cooling pipe (28) at a constant flow rate (240 ml/sec in this example), as maintained at a given uniform temperature (9±0.5° C.) by cooler (24). An obtained double capsule is sent to a separator (60 meshes) by the cooling liquor, dried and washed. The obtained soft capsule has an average outside diameter of 8 mm and inner capsule diameter of 5 mm. The content of the every soft capsule is as follows:

| Inner capsule liquor | 60 mg (average) |
| --- | --- |
| Inner film-forming liquor | 10 mg (average) |
| Outer capsule liquor | 120 mg (average) |
| Outer film-forming liquor | 46 mg (average) |

What is claimed is:

1. A double soft capsule wherein an inner soft capsule containing an oil therein and having a water-soluble film containing gelatin and sorbite thereon is contained with outer capsule oil in an outer soft capsule having a water-soluble film containing gelatin and sorbite thereon, said inner soft capsule having a diameter of at least 2 mm and said outer soft capsule having a diameter of at least 6 mm.

2. A double soft capsule according to claim 1, wherein the contents of gelatin and sorbite are 60 to 90 weight % and 40 to 10 weight %, respectively, based on the total weight of the film.

3. A double soft capsule according to claim 1 having a double capsule structure so that the outer soft capsule is soluble at the stomach and the inner soft capsule is soluble at the intestine.

4. A double soft capsule according to claim wherein the inner soft capsule oil comprises Vitamin $B_2$, and the outer soft capsule oil comprises Vitamin E.

* * * * *